United States Patent [19]

Kukolja et al.

[11] 4,302,391
[45] Nov. 24, 1981

[54] UNSYMMETRICAL AZETIDINONE ALDEHYDE DISULFIDES AND PROCESS

[75] Inventors: Stjepan Kukolja, Carmel; Janice L. Pfeil, Indianapolis, both of Ind.

[73] Assignee: Eli Lilly and Company, Indianapolis, Ind.

[21] Appl. No.: 137,861

[22] Filed: Apr. 7, 1980

[51] Int. Cl.$^3$ .............. C07D 205/08; C07D 498/04; C07D 403/12; C07D 405/12
[52] U.S. Cl. .............. 260/239 A; 260/245.4; 260/330.3; 260/347.3; 544/90
[58] Field of Search ............ 260/239 A, 330.3, 347.4, 260/245.4

[56] References Cited

U.S. PATENT DOCUMENTS

| | | | |
|---|---|---|---|
| 3,872,086 | 8/1975 | Barton et al. | 260/239 A |
| 3,954,732 | 5/1976 | Kamiya et al. | 424/271 |
| 4,066,641 | 1/1978 | Hamashima | 260/239 A |
| 4,071,513 | 1/1978 | Kim | 260/239 A |

OTHER PUBLICATIONS

Barton et al., Chem. Comm., 1137 (1971).
Kamiya et al., Tet. Letters, 13001 (1973).
Kim et al., Tet. Letters, 409 (1978).
Yoshida et al., Chem. Pharm. Bull. 24, 362 (1976); 25, 2082 (1977).
Glaxo, Chem. Abs. 91, 157730q, (1979).
Woodward et al., Chem. Abs. 90, 54804s.

*Primary Examiner*—Mark L. Berch
*Attorney, Agent, or Firm*—William B. Scanlon; Arthur R. Whale

[57] ABSTRACT

Aryl 4R[1-(2-N-3-methyl-4-al-Z-but-2-ene-oate)-2-oxo-3S-acylamino azetidinone]disulfides are prepared by reacting the corresponding 7α-acylamino-2α-alkoxy-3-methyl-3-cephem-4-carboxylates first with either phenylsulfenyl chloride or a monosubstituted-phenylsulfenyl chloride where the substituent is either chloro, methoxy, methyl or acetoxy. The disulfide compounds produced in this invention are intermediates in the synthesis of the 7β-acylamino-7α-alkoxy-3-methyl 1-oxa β-lactam acids, a class of antibiotic compounds.

14 Claims, No Drawings

UNSYMMETRICAL AZETIDINONE ALDEHYDE DISULFIDES AND PROCESS

BACKGROUND OF THE INVENTION 1-oxa β-lactam compounds, which possess the following general structure:

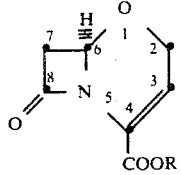

have recently been the subject of extensive research efforts due to their antibacterial activity. Specifically, there have been some recent reports of syntheses of 1-oxa β-lactam compounds substituted with methyl at the C-3 position. For example, Naylor et al. in "Recent Advances in the Chemistry of β-Lactam Antibiotics" (J. Elks, ed.), The Chemical Society, London, 1977, p. 204, reported a synthesis of 1-oxacephalexin. Similarly, Narisada et al., *Heterocycles*, 7, 839 (1977), were able to prepare several 3-methyl 1-oxa β-lactam compounds which exhibited antibacterial activity from four to eight times greater than the corresponding cephalosporins. The present invention describes and claims novel intermediates which can be employed in the synthesis of the aforementioned biologically active 7β-acylamino-7α-alkoxy-3-methyl 1-oxa-β-lactam compounds. The process for the preparation of such intermediates is an alternate aspect of the present invention.

SUMMARY OF THE INVENTION

This invention is directed to aryl 4R[1(2-N-3-methyl-4-al-Z-but-2-ene-oate)-2-oxo-3S-acylamino azetidine]disulfide compounds (referred to herein as unsymmetrical azetidinone aldehyde disulfide compounds), and to a method for their preparation. According to the process of this invention, a 7α-acylamino-2α-alkoxy-3-methyl-3-cephem-4-carboxylate cephalosporin is reacted in inert aromatic hydrocarbon or chlorinated hydrocarbon solvent with between about 0.8 to about 1.2 equivalents of either phenylsulfenyl chloride or monosubstituted-phenylsulfenyl chloride per equivalent of the cephalosporin starting material at a temperature between about 0° C. and about ambient temperature. The desired disulfide compound can be isolated by the standard chromatographic or crystallization techniques.

The novel disulfide compounds produced by the process of the invention are useful as intermediates in the synthesis of a particular class of biologically active 1-oxa β-lactam antibiotics. Specifically, an unsymmetrical disulfide aldehyde azetidinone compound of the invention is first reduced to the corresponding alcohol, and then cyclized to provide the desired 1-oxa β-lactam nucleus. This nucleus is then α-methoxylated at the C-7 position and the carboxylic acid protecting group is subsequently removed to give the biologically active 7β-acylamino-7α-alkoxy-3-methyl 1-oxa β-lactam compounds.

DETAILED DESCRIPTION OF THE INVENTION

This invention is directed to compounds of the following general formula I;

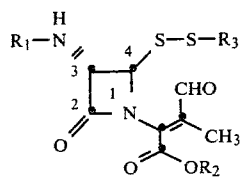

and the process for their preparation. These compounds are referred to in this application, for convenience sake, as "unsymmetrical azetidinone aldehyde disulfide" compounds. In the above term, "unsymmetrical" refers to the presence of different moieties (ie., a substituted azetidinone ring and a substituted or unsubstituted phenyl ring) bonded to either end of the same disulfide group, and "aldehyde" calls attention to the aldehyde group on the side chain attached to the azetidinone nitrogen, emphasizing that this aldehyde group is not the alcohol function required for cyclization of the molecule to a 1-oxa β-lactam compound.

When the reduction of the aldehyde group to the alcohol group is accomplished, the resultant compounds are referred to as the "unsymmetrical azetidinone alcohol disulfide" compounds.

The 1-oxa β-lactam antibiotics obtained from the azetidinone disulfides of this invention possess the following bicyclic ring system:

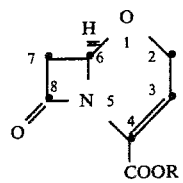

wherein R can be hydrogen or a conventional carboxylic acid protecting group.

In the formulas contained in this application, the mark "◂" means β-configuration and the dotted line "⊥⊥⊥⊥" means α-configuration.

The azetidinone aldehyde disulfide compounds of this invention are represented by the following general formula I

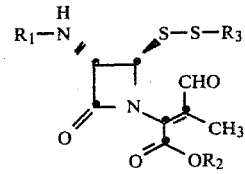

wherein $R_1$ is an acyl group of the formula

wherein R' is (a) $C_1$–$C_7$ alkyl, cyanomethyl, $C_1$–$C_6$ haloalkyl, 4-protected amino-4-protected carboxybutyl; or
(b) $C_1$–$C_6$ alkoxy, phenoxy, benzyloxy or 4-methoxybenzyloxy; or
(c) the group —R″ wherein R″ is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; or
(d) an arylalkyl group of the formula R″—(O)$_m$—CH$_2$— wherein R″ is as defined above, and m is 0 or 1; or
(e) a substituted arylalkyl group of the formula

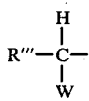

wherein R‴ is R″ as defined above, 2-thienyl, 3-thienyl, 2-furyl or 3-furyl; W is protected hydroxy, protected carboxy, protected amino, or
(f) a heteroarylmethyl group of the formula R″″—CH$_2$— wherein R″″ is 2-thienyl, 3-thienyl, 2-furyl, 3-furyl, 2-thiazolyl, 5-tetrazolyl, 1-tetrazolyl;

$R_2$ is a carboxy protecting group and $R_3$ is phenyl or a mono substituted phenyl group, where the substituents are chloro, methoxy, methyl, or acetoxy.

In the following specification, the protecting group designation is omitted for simplicity in nomenclature, but it is understood that, in the description of the process of this invention, each carboxy, hydroxy or amino group is a protected group.

In the foregoing definitions of the compounds of this invention, the term "$C_1$–$C_7$ alkyl" refers to methyl, ethyl, n-propyl, n-butyl, isobutyl, pentyl, n-hexyl, cyclohexyl, n-heptyl and like aliphatic hydrocarbon chains.

The term "$C_1$–$C_6$ haloalkyl" refers to chloromethyl, bromomethyl, iodomethyl, 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

The term, "protected amino" as employed in the above definition has reference to an amino group substituted with one of the commonly employed amino blocking groups such as the tert-butoxycarbonyl group (t-BOC), the benzyloxycarbonyl group, the 4-methoxybenzyloxycarbonyl group, the 2,2,2-trichloroethoxycarbonyl group, the trimethylsilyl group, and like amino protecting groups. The nature of such amino protecting groups is not critical so long as the protected amino functionality is stable under the reaction conditions described hereinafter.

The term "protected hydroxy" has reference to any group stable under the reaction conditions of the subsequent step in this synthesis of the 1-oxa β-lactam compounds, but readily cleavable thereafter. Such groups include the formyloxy group, the chloroacetoxy group, the benzhydryloxy group, the trityloxy group, the trimethylsilyl group, and the like.

The term "carboxy protecting group" or "protecting carboxy" has reference to a carboxy group which has been esterified with one of the commonly used carboxylic acid protecting ester groups employed to block or protect the carboxylic acid functionality while reactions involving other functional sites of the compound are carried out. Such protected carboxy groups are noted for their ease of cleavage by hydrolytic methods to the corresponding carboxylic acid. Examples of carboxylic acid protecting groups include tert-butyl, p-methoxybenzyl, diphenylmethyl, 2,4,6-trimethylbenzyl, trityl, 4-methoxytrityl, 4,4′-dimethoxytrityl, 4,4′,4″-trimethoxytrityl and like ester forming moieties. The nature of such ester forming groups is not critical so long as the ester formed therewith is stable under the reaction conditions described hereinafter. Preferred carboxylic acid protecting groups are diphenylmethyl, 4-methoxybenzyl, and tert-butyl.

In the foregoing definitions, hydroxy, amino, and carboxy protecting groups are not exhaustively defined. The function of such groups is to protect the reactive functional groups during the preparation of the desired products and then to be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

When in the above definition R″ represents a substituted phenyl group, R″ can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a cyanophenyl group, for example 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R″ represents disubstituted phenyl groups wherein the substituents can be different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

Illustrative of the acyl groups,

where R′ is $C_1$–$C_7$ alkyl, or $C_1$–$C_6$ haloalkyl, are acetyl, propionyl, butyryl, hexanoyl, chloroacetyl, bromoacetyl and the like.

Representative of the acyl groups

when R′ is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-protected aminobenzoyl.

Illustrative of the acyl groups

when R' is a group of the formula R''—(0)$_m$—CH$_2$—, m is 0 and R'' is phenyl or substituted phenyl, are phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 3,4-dimethoxyphenylacetyl and the like; and when m is 1, representative groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenylacetyl, 3,4-dimethylphenoxyacetyl, 4-isopropylphenoxyacetyl, 3-cyanophenoxyacetyl and like substituted phenoxyacetyl groups.

Illustrative of the acyl groups when R' is a substituted arylalkyl group of the formula

are the carboxy substituted acyl groups such as the 2-carboxyl-2-phenylacetyl group of the formula

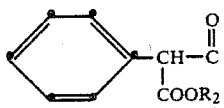

and similar groups wherein the phenyl ring is substituted, for example, 2-carboxy-2-(4-chlorophenyl)acetyl, 2-carboxy-2-(4-methoxyphenyl)acetyl, 2-carboxy-2-(2-thienyl)acetyl, 2-carboxy-2-(4-methylphenyl)acetyl, 2-carboxy-2-(4-(carboxymethyl)phenyl)acetyl, 2-carboxy-2-(4-(hydroxymethyl)phenyl)acetyl and like groups.

Representative of the acyl groups when R' is a hydroxy substituted arylalkyl group are 2-hydroxy-2-(4-methoxyphenyl)acetyl, 2-hydroxy-2-(3-chloro-4-hydroxyphenyl)acetyl, 2-hydroxy-2-(3-bromophenyl)acetyl, 2-hydroxy-2-(3,5 dichloro-4-hydroxyphenyl)acetyl, 2-hydroxy-2-(3-chloro-4-methoxyphenyl)acetyl, 2-hydroxy-2-(3-chlorophenyl)acetyl, 2-hydroxy-2-(4-aminomethylphenyl)acetyl, 2-hydroxy-2-(3-thienyl)acetyl.

When R' is an amino substituted arylalkyl group, acyl groups represented thereby include 2-amino-2-phenylacetyl, 2-amino-2-(4-cyanophenyl)acetyl, 2-amino-2-(4-hydrophenyl)acetyl, and like groups.

Representative of the acyl group

when R' is a heteroarylmethyl group of the formula R''''-CH$_2$- are 2-thienylacetyl, 3-thienylacetyl, 2-furylacetyl, 2-thiazolylacetyl, 1-tetrazolylacetyl, 5-tetrazolylacetyl and the like.

When in the above definition R$_3$ is a monosubstituted phenyl group where the substituents are chloro, methoxy, methyl or acetoxy, the substituent can be in the ortho, meta or para position. Such substituted R$_3$ groups include 4-chlorophenyl, 2-chlorophenyl, 4-methoxyphenyl, 3-methoxyphenyl, 4-methylphenyl, 2-methylphenyl, 4-acetoxyphenyl, 3-acetoxyphenyl and the like.

The process for preparing the compounds represented by general formula I, comprises reacting a 7α-acylamino-2α-alkoxy-3-methyl-3-cephem-4-carboxylate with an arylsulfenyl chloride to give the desired azetidinone aldehyde disulfide compound. The process is illustrated by the following generalized reaction scheme:

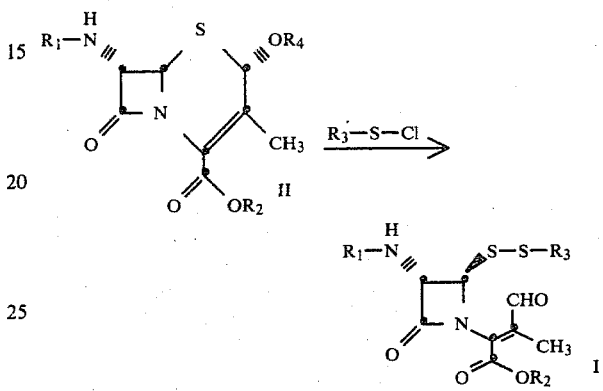

In the above general formula II R$_1$, R$_2$, and R$_3$ are as described for general formula I, and R$_4$ is methyl, ethyl or isopropyl.

Specifically, the process of this invention is carried out by adding the 7α-alkoxy-2α-alkoxy-3-methyl-3-cephem-4-carboxylate cephalosporin to a solution of at least 1 equivalent of the arylsulfenyl chloride per mole of the cephalosporin in a chlorinated hydrocarbon solvent or an aromatic hydrocarbon solvent. Alternatively, the sulfenyl chloride can be added to a solution of the 7α-alkoxy-2α-alkoxy-3-methyl-3-cephem-4-carboxylate cephalosporin in a chlorinated hydrocarbon solvent or an aromatic hydrocarbon solvent. The reaction solution is stirred until the sulfenation reaction is complete. The course of the sulfenation reaction can be followed by thin layer chromatography. For example, a small portion of the reaction mixture can be removed from time to time and a comparative thin layer chromatography run with starting material and product. After completion, the sulfenation reaction solution is evaporated to dryness, redissolved, then washed successively with sodium bicarbonate solution, hydrochloric acid, water and sodium chloride solution and can be used as is or further purified by conventional column chromatography techniques.

The arylsulfenyl chloride used in the process claimed in this application can be prepared, without isolation, immediately before it is used, as the examples in this application describe, or it can be prepared and isolated beforehand for use at some later time in the process of this application.

The process of this invention can be performed at a temperature between about 0° C. and about 30° C. Preferably the reaction is carried out at temperatures between about 0° C. and about 10° C.

Although at least 1 molar equivalent of arylsulfenyl chloride is required for complete conversion, it is preferable to employ between about 1 to about 1.2 moles of the arylsulfenyl chloride reagent per mole of the cephalosporin starting material.

The process of this invention is preferably carried out under substantially anhydrous conditions, ie., under a dried inert atmosphere (such as nitrogen) using a previously dried aromatic hydrocarbon or chlorinated hydrocarbon solvent. The anhydrous conditions, however, are not essential to the process of this invention, such that the reaction will occur without anhydrous conditions, although at lower yields than if anhydrous conditions are used.

As mentioned above, the process of this invention is carried out either in a halogenated hydrocarbon solvent or an aromatic hydrocarbon solvent. Chlorinated hydrocarbon solvents which can be employed include methylene chloride, chloroform, dichloroethane, trichloroethane, chlorobenzene, carbon tetrachloride, 1,1-dibromo-2-chloroethane and the like. Aromatic hydrocarbon solvents include benzene, toluene, xylene and the like. Methylene chloride is the preferred solvent in this process.

For example, a methylene chloride solution of a 7α-acylamino-2α-alkoxy-3-methyl-3-cephem-4-carboxylate substrate compound is combined in a one to one molar ratio with an arylsulfenyl chloride in methylene chloride at 0° C. This solution is agitated with stirring at 0° C. for 45 minutes then for additional 15 minutes with the cooling bath removed. The methylene chloride is evaporated, the resulting residue is dissolved in ethyl acetate, added to a sodium bicarbonate solution which is agitated by stirring for 15 minutes at room temperature. The ethyl acetate layer is then separated and is washed successively with 1 molar hydrochloric acid, water and sodium chloride solution. The ethyl acetate is then evaporated and the resulting residue is chromatographed on silica gel.

A preferred group of 7α-acylamino-2α-alkoxy-3-methyl-3-cephem-4-carboxylates which can be converted to the unsymmetrical azetidinone aldehyde disulfide compounds according to the process of this invention are represented by the following general formula II

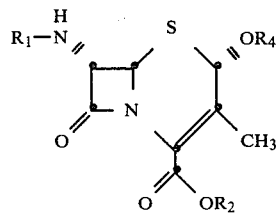

wherein $R_1$ is an acyl group of the formula

wherein R' is
(a) $C_1$–$C_7$ alkyl, or cyanomethyl
(b) $C_1$–$C_6$ alkoxy
(c) an arylalkyl group of the formula

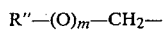

wherein R'' is phenyl or substituted phenyl wherein the substituents are 1 or 2 halogens, hydroxy, cyano, trifluoromethyl, $C_1$–$C_4$ alkyl, $C_1$–$C_4$ alkoxy, carboxy, carboxymethyl, hydroxymethyl or aminomethyl; and m is 0 or 1,
(d) 2-thienylmethyl, 3-thienylmethyl 2-furylmethyl, 3-furylmethyl, 2-thiazolylmethyl, 5-tetrazolylmethyl, 1-tetrazolylmethyl;
(e) 1-hydroxy-1-phenylmethyl, 1-amino-1-phenylmethyl, 1-amino-1-(4-hydroxyphenyl)methyl;

$R_4$ is methyl, ethyl or isopropyl; and $R_2$ is diphenylmethyl, tert-butyl or 4-methoxybenzyl.

Illustrative compounds described above which can be employed as starting materials in the process of this invention include the following 7α-acylamino-2α-alkoxy-3-methyl-3-cephem-4-carboxylates:
diphenylmethyl 7α-octamido-2α-methoxy-3-methyl-3-cephem-4-carboxylate,
diphenylmethyl 7α-cyanoacetamido-2α-methoxy-3-methyl-3-cephem-4-carboxylate,
diphenylmethyl 7α-[2-(2-thienyl)acetamido]-2α-methoxy-3-methyl-3-cephem-4-carboxylate,
tert-butyl 7α-[2-(2-furyl)acetamido]-2α-methoxy-3-methyl-3-cephem-4-carboxylate,
p-methoxybenzyl 7α-benzamido-2α-methoxy-3-methyl-3-cephem-4-carboxylate,
p-methoxybenzyl 7α-phenylacetamido-2α-isopropoxy-3-methyl-3-cephem-4-carboxylate,
diphenylmethyl 7α-phenoxyacetamido-2α-methoxy-3-methyl-3-cephem-4-carboxylate,
diphenylmethyl 7α-phenoxyacetamido-2α-isopropoxy-3-methyl-3-cephem-4-carboxylate,
diphenylmethyl 7α-phenylacetamido-2α-methoxy-3-methyl-3-cephem-4-carboxylate,
p-methoxybenzyl 7α-(2-tert-butoxycarbonylaminophenylacetamido)-2α-methoxy-3-methyl-3-cephem-4-carboxylate,
diphenylmethyl 7α-(2-(tert-butoxycarbonylamino)-2-(4-benzylcarbonatophenyl)acetamido)-2α-methoxy-3-methyl-3-cephem-4-carboxylate,
diphenylmethyl 7α-(2-(1-tetrazolyl)acetamido)-2α-methoxy-3-methyl-3-cephem-4-carboxylate,
tert-butyl 7α-(2-(2-thiazolyl)acetamido)-2α-methoxy-3-methyl-3-cephem-4-carboxylate,
diphenylmethyl 7α-(2-benzylcarbonato-2-phenylacetamido)-2α-methoxy-3-methyl-3-cephem-4-carboxylate.

More preferred 7α-acylamino-2α-alkoxy-3-methyl-3-cephem-4-carboxylate which can be used as substrates in the process of this invention are represented by the above structural formula II wherein
(a) $R_1$ is an acyl group of the formula

wherein $R_5$ is an arylalkyl group of the formula

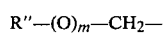

wherein R'' is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; m is 0 or 1,
(b) $R_3$ is methyl,
(c) and $R_2$ is diphenylmethyl, methoxybenzyl, or tert-butyl.

Some examples of these compounds include:

diphenylmethyl 7α-phenylacetamido-2α-methoxy-3-methyl-3-cephem-4-carboxylate,
p-methoxyphenyl 7α-phenoxyacetamido-2α-methoxy-3-methyl-3-cephem-4-carboxylate,
diphenylmethyl 7α-(4-chlorophenylacetamido)-2α-methoxy-3-methyl-3-cephem-4-carboxylate,
diphenylmethyl 7α-(2-chlorophenylacetamido)-2α-methoxy-3-methyl-3-cephem-4-carboxylate,
diphenylmethyl 7α-(4-trifluoromethylphenylacetamido)-2α-methoxy-3-methyl-3-cephem-4-carboxylate,
diphenylmethyl 7α-(4-benzylcarbonatophenylacetamido)-2α-methoxy-3-methyl-3-cephem-4-carboxylate,
p-methoxybenzyl 7α-(2-(p-methoxybenzyloxy)-carbonylphenylacetamido)-2α-methoxy-3-methyl-3-cephem-4-carboxylate,
diphenylmethyl 7α-(p-methoxyphenylacetamido)-2α-methoxy-3-methyl-3-cephem-4-carboxylate,
diphenylmethyl 7α-(p-methylphenylacetamido)-2α-methoxy-3-methyl-3-cephem-4-carboxylate.

A preferred group of unsymmetrical aldehyde disulfide compounds described by this invention are represented by the following general formula

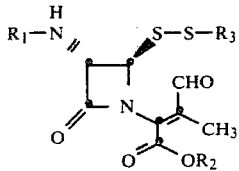

wherein $R_1$ is an acyl group of the formula

wherein R' is
(a) $C_1$-$C_7$ alkyl, cyanomethyl;
(b) $C_1$-$C_6$ alkoxy
(c) benzyl, 1-phenoxymethyl, 1-p-methoxyphenylmethyl,
(d) 2-thienylmethyl, 3-thienylmethyl 2-furylmethyl, 3-furylmethyl, 2-thiazolylmethyl, 5-tetrazolylmethyl, 1-tetrazolylmethyl;
(e) 1-protected hydroxy-1-phenylmethyl, 1-protected amino-1-phenylmethyl, 1-protected amino-1-(4-protected hydroxyphenyl)methyl, $R_2$ is tert-butyl, p-methoxybenzyl or diphenylmethyl, and $R_3$ is phenyl or a mono-substituted phenyl, where the substituents are chloro, methoxy, methyl or acetoxy.

Illustrative of the preferred compounds of the invention, and hence the preferred group of substrates for the process of this invention include the following unsymmetrical azetidinone aldehyde disulfide compounds:
phenyl 4R[1-(diphenylmethyl 2-N-3-methyl-4-al-Z-but-2-ene-oate)-2-oxo-3S-phenylacetamido azetidine]-disulfide,
p-methylphenyl 4R[1-(diphenylmethyl 2-N-3-methyl-4-al-Z-but-2-ene-oate)-2-oxo-3S-phenylacetamido azetidine]-disulfide,
o-chlorophenyl 4R[1-(tert-butyl 2-N-3-methyl-4-al-Z-but-2-ene-oate)-2-oxo-3S-phenylacetamido azetidine]disulfide,
p-methoxyphenyl 4R[1-(p-methoxybenzyl 2-N-3-methyl-4-al-Z-but-2-ene-oate)-2-oxo-3S-phenylacetamido azetidine]disulfide,
p-acetoxyphenyl 4R[1-(diphenylmethyl 2-N-3-methyl-4-al-Z-but-2-ene-oate)-2-oxo-3S-phenylacetamido azetidine]disulfide,
phenyl 4R[1-(diphenylmethyl 2-N-3-methyl-4-al-Z-but-2-ene-oate)-2-oxo-3S-phenoxyacetamido azetidine]-disulfide,
p-methylphenyl 4R[1-(diphenylmethyl 2-N-3-methyl-4-al-Z-but-2-ene-oate)-2-oxo-3S-phenoxyacetamido azetidine]disulfide,
p-chlorophenyl 4R[1-(tert-butyl 2-N-3-methyl-4-but-2-ene-oate)-2-oxo-3S-phenoxyacetamido azetidine]disulfide,
o-methoxyphenyl 4R[1-(p-methoxybenzyl 2-N-3-methyl-4-al-Z-but-2-ene-oate)-2-oxo-3S-phenoxyacetamido azetidine]disulfide,
p-acetoxyphenyl 4R[1-(diphenylmethyl 2-N-3-methyl-4-al-Z-but-2-ene-oate)-2-oxo-3S-phenoxyacetamido azetidine]disulfide,
phenyl 4R[1-(diphenylmethyl 2-N-3-methyl-4-al-Z-but-2-ene-oate)-2-oxo-3S-(2-(2-thienyl)acetamido) azetidine]disulfide,
p-chlorophenyl 4R[1-(tert-butyl 2-N-3-methyl-4-al-Z-but-2-ene-oate)-2-oxo-3S-(2-(2-thienyl)-acetamido) azetidine]disulfide,
m-chlorophenyl 4R[1-(p-methoxybenzyl 2-N-3-methyl-4-al-Z-but-2-ene-oate)-2-oxo-3S-(2-(2-thiazolyl)-acetamido) azetidine]disulfide,
p-methoxy 4R[1-(diphenylmethyl 2-N-3-methyl-4-al-Z-but-2-ene-oate)-2-oxo-3S-(2-(2-thiazolyl)-acetamido) azetidine]disulfide,
o-methoxy 4R[1-(tert-butyl 2-N-3-methyl-4-al-Z-but-2-ene-oate)-2-oxo-3S-(2-(1-tetrazolyl)acetamido) azetidine]disulfide,
p-acetoxyphenyl 4R[1-(p-methoxybenzyl 2-N-3-methyl-4-al-Z-but-2-ene-oate)-2-oxo-3S-(2-(1-tetrazolyl)acetamido) azetidine]disulfide,
o-acetoxyphenyl 4R[1-(diphenylmethyl 2-N-3-methyl-4-al-Z-but-2-ene-oate)-2-oxo-3S-(2-(2-furyl)-acetamido) azetidine]disulfide,
phenyl 4R[1-(tert-butyl 2-N-3-methyl-4-al-Z-but-2-ene-oate)-2-oxo-3S-(2-(2-furyl)acetamido) azetidine]disulfide,
phenyl 4R[1-(p-methoxybenzyl 2-N-3-methyl-4-al-Z-but-2-ene-oate)-2-oxo-3S-cyanoacetamido azetidine]-disulfide,
p-chlorophenyl 4R[1-(diphenylmethyl 2-N-3-methyl-4-al-Z-but-2-ene-oate)-2-oxo-3S-cyanoacetamido azetidine]disulfide,
o-chlorophenyl 4R[1-(tert-butyl 2-N-3-methyl-4-al-Z-but-2-ene-oate)-2-oxo-3S-(2-benzylcarbonato-2-phenylacetamido azetidine]disulfide,
p-methoxyphenyl 4R[1-(p-methoxybenzyl 2-N-3-methyl-4-al-Z-but-2-ene-oate)-2-oxo-3S-(2-benzylcarbonato-2-phenylacetamido azetidine]disulfide, o-methoxybenzyl 4R[1-(diphenylmethyl 2-N-3-methyl-4-al-Z-but-2-ene-oate)-2-oxo-3S-(2-tert-butoxycarbonylamino-2-phenylacetamido) azetidine]disulfide,
p-methylphenyl 4R[1-(tert-butyl 2-N-3-methyl-4-al-Z-but-2-ene-oate)-2-oxo-3S-(2-tert-butoxycarbonylamino-2-phenylacetamido) azetidine]disulfide,
m-methylphenyl 4R[1-(p-methoxybenzyl 2-N-3-methyl-4-al-Z-but-2-ene-oate)-2-oxo-3S-(2-(tert-butoxycarbonylamino)-2-(4-benzylcarbonatophenyl)acetamido) azetidine]disulfide, p-acetoxyphenyl 4R[1-diphenylmethyl 2-N-3-methyl-4-al-Z-but-2-ene-oate)-2-oxo-3S-(2-(tert-butoxycarbonylamino)-2-(4-benzylcarbonatophenyl)acetamido) azetidine]disulfide, o-acetoxy 4R[1-(tert-butyl 2-N-3-methyl-4-al-Z-but-2-ene-oate)-2-oxo-3S-(2-benzyloxycarbonyl-2-phenylacetamido) azetidine]disulfide, phenyl 4R[1-(p-methoxybenzyl 2-N-3-methyl-4-al-Z-but-2-ene-oate)-2-oxo-3S-(2-benzyloxycarbonyl-2-phenylacetamido) azetidine]disulfide.

A more preferred group of unsymmetrical azetidinone aldehyde disulfide compounds of the invention are again represented by the following general formula

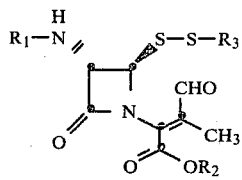

wherein $R_1$ is an acyl group of the formula

wherein R' is

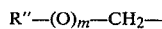

wherein R" is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; and m is 0 or 1, $R_2$ is tert-butyl, p-methoxybenzyl or diphenylmethyl and $R_3$ is phenyl or mono-substituted phenyl wherein the substituents are chloro, methoxy, methyl or acetoxy.

Illustrative of the more preferred compounds of this invention include the following azetidinone alcohol disulfide compounds:

phenyl 4R[1-(diphenylmethyl 2-N-3-methyl-4-al-Z-but-2-ene-oate)-2-oxo-3S-phenylacetamido azetidine]disulfide, p-methylphenyl 4R[1-(diphenylmethyl 2-N-3-methyl-4-al-Z-but-2-ene-oate)-2-oxo-3S-phenylacetamido azetidine]disulfide, o-chlorophenyl 4R[1-(tert-butyl 2-N-3-methyl-4-al-Z-but-2-ene-oate)-2-oxo-3S-phenylacetamido azetidine]disulfide, p-methoxyphenyl 4R[1-(p-methoxybenzyl 2-N-3-methyl-4-al-Z-but-2-ene-oate)-2-oxo-3S-phenylacetamido azetidine]disulfide, p-acetoxyphenyl 4R[1-(diphenylmethyl 2-N-3-methyl-4-al-Z-but-2-ene-oate)-2-oxo-3S-phenylacetamido azetidine]disulfide, phenyl 4R[1-(diphenylmethyl 2-N-3-methyl-4-al-Z-but-2-ene-oate)-2-oxo-3S-phenoxyacetamido azetidine]disulfide, p-methylphenyl 4R[1-(diphenylmethyl 2-N-3-methyl-4-al-Z-but-2-ene-oate)-2-oxo-3S-phenoxyacetamido azetidine]disulfide, p-chlorophenyl 4R[1-(tert-butyl 2-N-3-methyl-4-al-Z-but-2-ene-oate)-2-oxo-3S-phenoxyacetamido azetidine]disulfide, o-methoxyphenyl 4R[1-(p-methoxybenzyl 2-N-3-methyl-4-al-Z-but-2-ene-oate)-2-oxo-3S-phenoxyacetamido azetidine]disulfide, p-acetoxyphenyl 4R[1-(diphenylmethyl 2-N-3-methyl-4-al-Z-but-2-ene-oate)-2-oxo-3S-phenoxyacetamido azetidine]disulfide, phenyl 4R[1-diphenylmethyl 2-N-3-methyl-4-al-Z-but-2-ene-oate)-2-oxo-3S-(2-(p-methylphenyl)acetamido) azetidine]disulfide, p-chlorophenyl 4R[1-(tert-butyl 2-N-3-methyl 4-al-Z-but-2-ene-oate)-2-oxo-3S-(2-(p-methylphenyl)acetamido) azetidine]disulfide, m-chlorophenyl 4R[1-(p-methoxybenzyl 2-N-3-methyl-4-al-Z-but-2-ene-oate)-2-oxo-3S-(2-(p-methoxyphenyl)acetamido) azetidine]disulfide, p-methoxyphenyl 4R[1-(diphenylmethyl 2-N-3-methyl-4-al-Z-but-2-ene-oate)-2-oxo-3S-(2-(p-methoxyphenyl)acetamido) azetidine]disulfide, o-methoxyphenyl 4R[1-(tert-butyl 2-N-3-methyl-4-al-Z-but-2-ene-oate)-2-oxo-3S-(2-(4-benzylcarbonatophenyl)acetamido) azetidine]disulfide, p-methylphenyl 4R[1-(p-methoxybenzyl 2-N-3-methyl-4-al-Z-but-2-ene-oate)-2-oxo-3S-(2-(4-benzylcarbonatophenyl)acetamido) azetidine]disulfide, o-methylphenyl 4R[1-(diphenylmethyl 2-N-3-methyl-4-al-Z-but-2-ene-oate)-2-oxo-3S-(4-chlorophenylacetamido) azetidine]disulfide, p-acetoxyphenyl 4R[1-(tert-butyl 2-N-3-methyl-4-al-Z-but-2-ene-oate)-2-oxo-3S-(4-chlorophenylacetamido) azetidine]disulfide, o-acetoxyphenyl 4R[1-(p-methoxybenzyl 2-N-3-methyl-4-al-Z-but-2-ene-oate)-2-oxo-3S-(2-chlorophenylacetamido) azetidine]disulfide, phenyl 4R[1-(diphenylmethyl 2-N-3-methyl-4-al-Z-but-2-ene-oate)-2-oxo-3S-(2-chlorophenylacetamido) azetidine]disulfide, phenyl 4R[1-(tert-butyl 2-N-3-methyl-4-al-Z-but-2-ene-oate)-2-oxo-3S-(4-trifluoromethylphenylacetamido) azetidine]disulfide, p-chlorophenyl 4R[1-(p-methoxybenzyl 2-N-3-methyl-4-al-Z-but-2-ene-oate)-2-oxo-3S-(4-trifluoromethylphenylacetamido) azetidine]disulfide, o-chlorophenyl 4R-[1-(diphenylmethyl 2-N-3-methyl-4-al-Z-but-2-ene-oate)-2-oxo-3S-(2-(4-benzyloxycarbonylphenyl)acetamido) azetidine]disulfide, p-methoxyphenyl 4R[1-(tert-butyl 2-N-3-methyl-4-al-Z-but-2-ene-oate)-2-oxo-3S-(2-(4-benzyloxycarbonylphenyl)acetamido) azetidine]disulfide, o-methoxyphenyl 4R[1-(p-methoxybenzyl 2-N-3-methyl-4-al-Z-but-2-ene-oate)-2-oxo-3S-(2-(4-tert-butoxycarbonylaminomethylphenyl)acetamido) acetamido]-disulfide, p-methylphenyl 4R[1-(diphenylmethyl 2-N-3-methyl-4-al-Z-but-2-ene-oate)-2-oxo-3S-(2-(4-tert-butoxycarbonylaminomethylphenyl)acetamido) azetidine]disulfide, m-methylphenyl 4R[1-(tert-butyl 2-N-3-methyl-4-al-Z-but-2-ene-oate)-2-oxo-3S-(2-(4-cyanophenyl)acetamido) azetidine]disulfide, p-acetoxyphenyl 4R[1-(p-methoxybenzyl 2-N-3-methyl-4-al-Z-but-2-ene-oate)-2-oxo-3S-(2-(4-cyanophenyl)-acetamido) azetidine]disulfide.

The starting material utilized in the process of this invention is synthesized by first epimerizing the C-6 side chain of a penicillin sulfoxide from the β to the α conformation, followed by the rearrangement of the 6α-acylaminopenicillin sulfoxide to the corresponding 7α-acylamino-3-methyl cephalosporin. The final step in the synthesis of the starting material involves the 2α-alkoxylation of the above cephalosporin.

In this synthesis, the epimerization at the C-6 of the 6β-acylaminopenicillanate-1-sulfoxide to the 6α-acylaminopenicillanate-1-sulfoxide, represented by the following scheme:

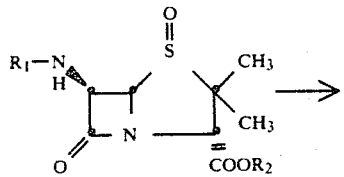

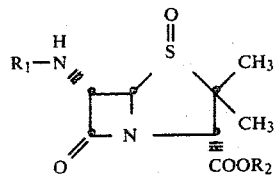

is a process well known to the those skilled in the art. See, for example, Ramsay and Stoodley, *Chemical Communications*, 1971, 450, Koppel, *Tetrahedron Letters*, 1973, 4233, Stoodley, U.S. Pat. No. 3,853,848, Clair et al., *J.C.S. Perkin Transactions* I, 937 (1973), and Barton et al., *J.C.S. Perkin Transactions* I, 599, 1973. The preferred method of epimerization at the C-6 position involves reacting the naturally occurring 6β-acylamino compound with equimolar amount of chlorotrimethylsilane in methylene chloride between about 0° C. and about ambient temperature, cooling the mixture to 0° C., and adding dropwise 2 moles of triethylamine per mole of penicillin sulfoxide substrate. The product can be purified by standard extraction and recrystallization techniques. The desired α-isomer can be isolated by dissolving the isomer mixture from the reaction mixture in a minimum quantity of ethyl acetate and adding a few crystals of the β-isomer. The β-isomer crystals are filtered, resulting in a filtrate containing substantially pure (approximately 90%) α-isomer of the penicillanate, which α-isomer can be isolated by evaporating the filtrate to dryness.

The preferred procedure of C-6 epimerization is described by Blaszczak in copending application Ser. No. 138,022, entitled "Process for Penicillin Epimerization", filed this even date.

The rearrangement of 6α-acylaminopenicillanate-1-sulfoxide to the corresponding 7α-acylamino-3-methyl-3-cephem-4-carboxylate, represented by the following general formula

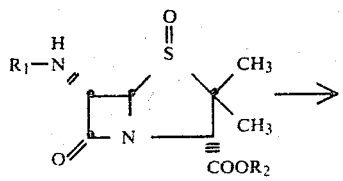

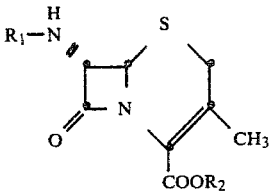

is analogous to a procedure also well known to those skilled in the art. Although several variations of the method are available to effect this rearrangement, the preferred method involves reacting the 6α-acylaminopenicillanate-1-sulfoxide with N,O-bis(trimethylsilyl)acetamide (BSA) and α-picoline.HBr in dried dioxane at reflux temperatures. The organic products of the reaction are then extracted into ethyl acetate, the ethyl acetate is evaporated and the extract is treated with neat pyridine. Pure 7α-acylamino-3-methyl-3-cephem-4-carboxylate can be obtained by recrystallization.

The procedure for the above rearrangement step was adapted from one described by Verweij et al., in U.S. Pat. No. 4,003,894.

The last step in the above general reaction scheme involves an α-alkoxylation at the C-2 position of the cephem moiety, the product of this reaction being the starting material of the process of the invention in the present application. This reaction is represented in the following general formula,

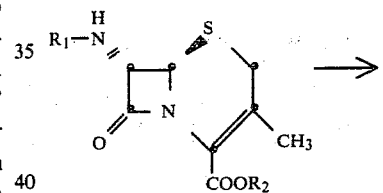

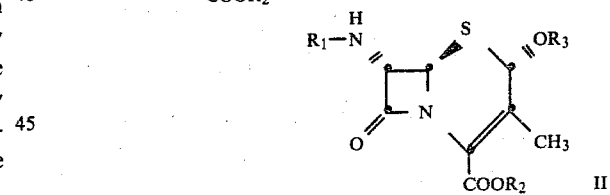
II

As with the above two steps in the synthesis of this starting material, the 2α-alkoxylation reaction involved at this stage of the synthesis is analogous to procedures well known to those skilled in the art; see, for example, D. O. Spry, *Tetrahedron Letters*, 3717 (1972); A. Yoshida, S. Oida, and E. Ohki, *Chemical and Pharmaceutical Bulletin of Japan* (Tokyo), 23, 2507 and 2518 (1975); ibid., 24 362 (1976); ibid., 25, 2082 (1977); C. O. Kim and P. A. McGregor, *Tetrahedron Letters*, 409 (1978). Although the aforementioned references describe various methods of 2α-alkoxylation for 7β-isomers of cephalosporins, the preferred method for the conversion of 7α-acylamino-3-methyl-3-cephem-4-carboxylate to its corresponding 2α-alkoxy analog comprises the addition of N-chlorosuccinimide to a solution of the substrate cephem compound dissolved in an appropriate alcohol and methylene chloride at room temperature. The desired 2α-alkoxy product can then be isolated by standard crystallization and chromatography techniques.

The compounds of this invention are intermediates useful in the preparation of a particular class of biologically active 1-oxa β-lactam compounds. The conversion of the unsymmetrical azetidinone aldehyde disulfide compounds to 3-methyl 1-oxa β-lactam antibiotics is accomplished by first reducing the unsymmetrical azetidinone aldehyde disulfide compounds to the corresponding alcohol compounds, followed by the cyclization of these alcohols to 7α-acylamino 1-oxa β-lactam compounds. These 1-oxa β-lactam compounds are then 7α-methoxylated followed by removal of the protecting group of the carboxylic acid function at C-4 to give the desired 7β-acylamino-7α-methoxy 1-oxa β-lactam antibiotic compounds.

As mentioned above, the first step of the synthesis of the desired antibiotic 1-oxa β-lactam compound involves reducing the unsymmetrical azetidinone aldehyde disulfide compounds, the compounds claimed in this application, with sodium cyanoborohydride to give the corresponding alcohol compounds. This reaction is represented by the general formula,

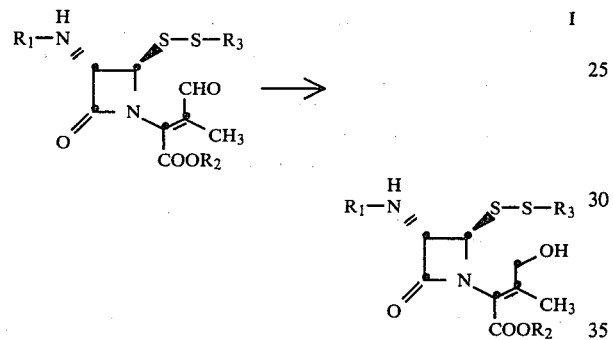

The procedure for this reduction is outlined generally in R. F. Borch, M. D. Dernstein, and H. D. Durat, *Journal of the American Chemical Society*, 93, 2897 (1971) and comprises of dissolving the aldehyde compound in aqueous tetrahydrofuran, acidifying the mixture, and then adding the sodium cyanoborohydride reducing agent. The desired alcohol can be purified by conventional extraction techniques.

The unsymmetrical azetidinone alcohol disulfide compounds are subsequently cyclized to give a 7α-acylamido-3-methyl 1-oxa β-lactam, represented by the following general formula,

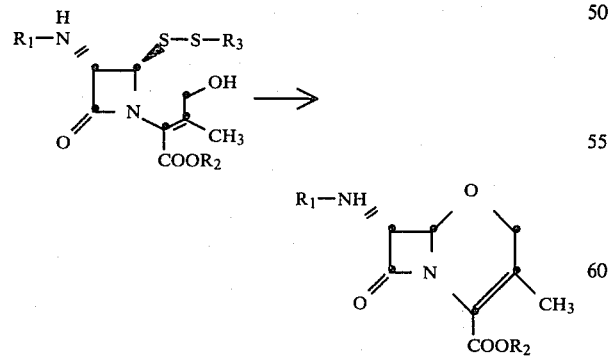

This cyclization is accomplished by reacting the alcohol compounds with a cyclization reagent selected from the group consisting of divalent mercury salts or phosphines. The divalent mercury salts are of the general formula Hg(X)$_2$, where X is chloro, bromo or trifluoroacetato. The mercury cyclization reagent and the substrate alcohol compound are reacted in a dry, polar, inert organic solvent such as acetonitrile. The phosphine cyclization reagent compounds have the general formula (R$_4$)$_3$P wherein R$_4$ can be alkyl, for example, methyl or ethyl, phenyl or substituted phenyl, for example, 4-methylphenyl. The phosphorus reagent and the substrate alcohol are reacted in a dry, inert, organic solvent such as 1,2-dichloroethane. The desired cyclized product obtained by the use of either class of cyclizing reagent can be purified by conventional chromatographic techniques.

The cyclization of the unsymmetrical azetidinone alcohol disulfide compounds to the corresponding 7α-acylamino-3-methyl 1-oxa β-lactam antibiotic is described by Kukolja and Pfeil in copending application Ser. No. 137,862, entitled "Azetidinone Alcohol Disulfides and Process for Cyclization", filed this even date.

The 7α-acylamino-3-methyl 1-oxa β-lactam ester compound are then converted to the 7β-acylamino-7α-methoxy-3-methyl 1-oxa β-lactam ester by reacting the 7α-acylamino substrate with lithium methoxide and tert-butyl hypochlorite. This reaction is represented generally by the following formula;

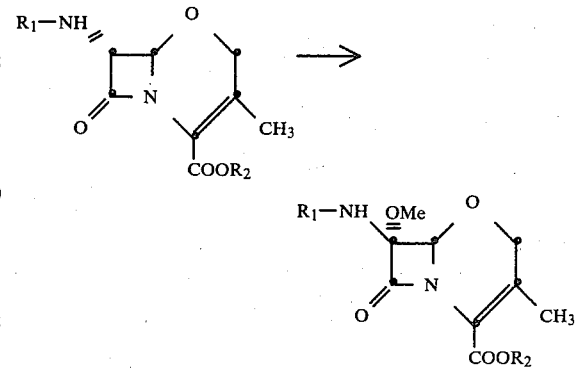

The reaction entails the addition of the 7α-acylamino 1-oxa β-lactam to a suspension of lithium methoxide in dry tetrahydrofuran in an inert atmosphere followed by addition of tert-butyl hypochlorite to the solution to initiate the methoxylation. Once the reaction has reached completion, the reaction is quenched with trimethylphosphite and glacial acetyl acid. The desired product can be isolated and purified with conventional liquid-liquid extraction techniques.

The above methoxylation of the 7α-acylamino 1-oxa β-lactam is carried out in a manner analogous to that of G. A. Koppel and R. E. Koehler, *Journal of the American Chemical Society*, 95, 2403 (1973).

The final step in the synthesis of a 1-oxa β-lactam from the claimed unsymmetrical azetidinone aldehyde disulfide compound is to remove the carboxylic acid protecting group from the 7β-acylamino-7α-methoxy 1-oxa-β-lactam ester as represented by this general formula,

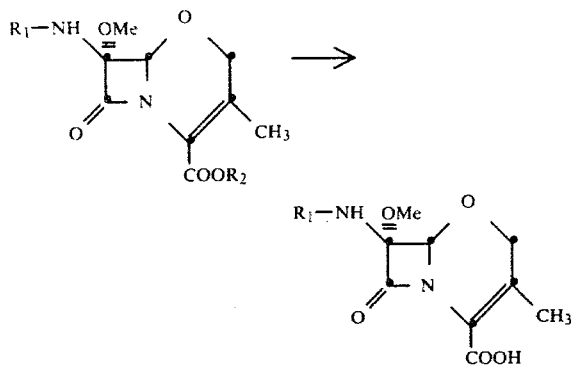

The deprotection step is well known to anyone skilled in the art. For example, to remove the diphenylmethyl carboxylic acid protecting group, the substrate diphenylmethyl carboxylate is dissolved in anisole and then treated with trifluoroacetic acid. The resultant 7β-acylamino-7α-methoxy-3-methyl 1-oxa-β-lactam acid is one example of 1-oxa β-lactam compounds that are prepared with the intermediates herein. Further examples of the removal of carboxy protecting group can be found in U.S. Pat. No. 4,138,486.

The following Examples (1-2) are provided to further illustrate this invention. Preparations 1 through 3 demonstrate a method of synthesizing the starting materials for the process of the invention, and preparations 4-8 demonstrate one method of converting the claimed compounds of this invention into biologically active 1-oxa β-lactam compounds. It is not intended that this invention be limited in scope by reason of any of the preparation or examples. In the following preparations and examples infrared absorption spectra, nuclear magnetic resonance spectra, ultraviolet absorption spectra and optical rotation spectra are abbreviated i.r., n.m.r., u.v and o.r., respectively. Only the i.r. absorption maxima attributable to the carbonyl function of the β-lactam ring are reported. The nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed as Hz.

EXAMPLE 1

Phenyl 4R[1-diphenylmethyl 2-N-3-methyl-4-al-Z-but-2-ene-oate)-2-oxo-3S-phenylacetamido azetidine]disulfide Phenylmercaptan (0.105 ml, 1 mmol) was added to a suspension of sodium bicarbonate (84 mg, 1 mmol) in methylene chloride (25 ml) at 0° C., and a 1 molar chlorine solution (1 ml, 1 mmol, methylene chlorine solution) was added to the solution. This reaction mixture was stirred for 2 hours at the end of which time a solution of diphenylmethyl 7α-phenylacetamido-2α-methoxy-3-methyl-3-cephem-4-carboxylate (528 mg, 1 mmol), in 10 ml of methylene chloride, was added to the reaction mixture. The reaction mixture was stirred for an additional 45 minutes at ice-bath temperatures and then for 15 minutes after the ice bath was removed. The solution was evaporated to dryness, the residue dissolved in ethyl acetate, and the solution added to an aqueous sodium bicarbonate solution. The solution was stirred for 15 minutes at room temperature, the aqueous layer separated, and the ethyl acetate layer was washed successively with 1 molar hydrochloric acid (1×), water (1×) and sodium chloride solution (1×). The solution was then evaporated to dryness, absorbed onto 2 grams of silica gel and chromatographed over 6 grams of silica gel, eluting successively with 100 ml of toluene, 100 ml of 5% ethyl acetate/toluene, 200 ml 8% ethyl acetate/toluene, and finally with 150 ml 12% ethyl acetate/toluene. The second fraction collected yielded the desired aldehyde, phenyl 4R[1-(diphenylmethyl 2-N-3-methyl-4-al-Z-but-2-ene-oate)-2-oxo-3S-phenylacetamido azetidine]disulfide (220 mg., 35% yield). i.r. (CHCl$_3$) 1785 cm$^{-1}$; n.m.r. (CDCl$_3$)δ1.73 (s, 3, CH$_3$), 3.52(s, 2, C$\underline{H}_2$Ph), 4.65 (dd, J=3 and 7 Hz, 1, C$_3$-H), 5.37 (d, J=3 Hz, 1, C$_4$-H), 6.17 (d, J=7 Hz, 1, NH), 7.02 (s, 1, C$\underline{H}$Ph$_2$), 7.20-7.50 (m, 20, aromatic protons), 9.35 (s, 1, aldehyde proton); u.v. (CH$_3$CN)λ$_{max}$=293 nm (ε=3,900).

EXAMPLE 2 p-Methylphenyl 4R[1-(diphenylmethyl 2-N-3-methyl-4-al-Z-but-2-ene-oate)-2-oxo-3S-phenylacetamido azetidine]disulfide Sodium bicarbonate (95 mg., 1.1 mmol) was suspended in 25 ml methylene chloride and the solution cooled to −20° C. A one molar methylene chloride solution of chlorine (1.1 ml, 1.1 mmol) was pipetted into the cooled sodium bicarbonate solution followed by the dropwise addition of a methylene chloride solution of p-methylphenylmercaptan (140 mg, 1.1 mmol dissolved in 5 ml of methylene chloride). The resultant solution was stirred at −20° C. for 0.5 hour, at the end of which time diphenylmethyl 7α-phenylacetamido-2α-methoxy-3-methyl-3-cephem-4-carboxylate (528 mg, 1 mmol) was added. The resultant solution was stirred at 0° C. for 0.5 hour, then evaporated to dryness. The residue was dissolved in ethyl acetate, and the solution was washed with sodium bicarbonate solution (2×), water (1×), sodium chloride solution (1×), dried over magnesium sulfate, filtered and evaporated to dryness. The yellow foam remaining after evaporation was absorbed onto 2.5 grams of silica and chromatographed over 7 grams of silica employing first 100 ml of toluene, then 100 ml 5% ethyl acetate in toluene and finally 150 ml of 10% ethyl acetate in toluene as the eluant. The last fraction collected yielded the desired aldehyde, p-methylphenyl 4R[1-(diphenylmethyl 2-N-3-methyl-4-al-Z-but-2-ene-2-oxo-3S-phenylacetamido azetidine] disulfide. (374 mg, 59% yield); i.r. (CHCl$_3$) 1780 cm$^{-1}$; n.m.r. (CDCl$_3$)δ1.73 (s, 3, CH$_3$), 2.20 (s, 3, toluyl CH$_3$), 3.48 (s, 2, C$\underline{H}_2$Ph), 4.68 (dd, J=3 and 8 Hz, 1, C$_3$-H), 5.35 (d, J=3 Hz, 1, C$_4$-H, 6.38 (d, J=8 Hz, 1, NH), 7.00 (s, 1, C$\underline{H}$Ph$_2$), 6.8-7.6 (m, 19, aromatic protons), 9.32 (s, 1, aldehydic proton); u.v. (CHCl$_3$) λ$_{max}$=294 nm (ε=5,500).

PREPARATION 1

Benzyl 6α-phenylacetamidopenicillanate-1-sulfoxide

Benzyl 6β-phenylacetamidopenicillanate-1-sulfoxide (8.80 g, 20 mmol.) was dissolved in 17 ml of methylene chloride under a positive nitrogen pressure, and the resultant solution was cooled to 2° C. in an ice water bath. Triethylamine (6.1 ml, 43.8 mmol) was added to the cooled solution, which resulted in the precipitation of the penicillanate. Thirteen more ml of methylene chloride was added to the solution to dissolve the penicillanate, followed by the addition of chlorotrimethylsilane (2.8 ml, 22 mmol). The reaction solution was stirred for 1 hour at 0° C., allowed to warm to ambient temperature and stirred for 1.5 hours longer, at the end of which time more chlorotrimethylsilane (1 ml, 7.86 mmol) was added and the stirring was continued for an additional 45 minutes. After cooling the reaction mixture to 4° C., acetic acid (3 ml, 52 mmol) was added dropwise, followed by addition of methylene chloride (20 ml). The reaction solution was then washed with 1 molar hydrochloric acid (3×) and with a saturated sodium bicarbonate solution (2×). The layers were separated, and the water layer was extracted with methylene chloride (1×). The methylene chloride layers were combined, washed with a saturated sodium chloride solution (1×) then dried over magnesium sulfate, filtered and evaporated to dryness. The resultant off-white foam (8.3 g) was recrystallized from a 1:1 mixture of ethyl acetate/cyclohexane. Five grams of the crystallized product was dissolved in 13 ml of ethyl acetate, and seeded with benzyl 6β-phenylacetamidopencillanate-1-sulfoxide crystals, to yield white crystals of the β isomer of the penicillanate (760 mg). The crystals of the β-isomer of the penicillanate of benzyl 6-phenylacetamidopenicillanate-1-sulfoxide were filtered off and the filtrate yielded predominantly pure (approximately 90%) α-isomer of benzyl 6-phenylacetamidopenicillanate-1-sulfoxide. (4.06 g, 46% yield). n.m.r. (d$_5$-pyridine) δ 1.13, 1.62 (s, 6, C(CH$_3$)$_2$), 3.78 (s, 2, COCH$_2$Ph), 4.92 (s, 1, C$_3$-H), 5.22 (br s, 2, CO$_2$CH$_2$Ph), 5.52 (d, J=2 Hz, 1, C$_5$-H), 5.88 (dd, J=2 and 8 Hz, 1, C$_6$-H), 7.33 (m, 10, aromatic), 10.13 (d, J=8 Hz, 1, NH).

PREPARATION 2

Benzyl 7α-phenylacetamido-3-methyl-3-cephem-4-carboxylate

To a solution of benzyl 6α-phenylacetamidopenicillanate-1-sulfoxide (31.4 g, 71.6 mmole) in dried dioxane (500 ml) was added N,O-bis[trimethylsilyl]acetamide (BSA) (39 ml, 158 mmole) and 58 ml of an α-picoline.HBr solution (1.23 M in CH$_2$Cl$_2$, 71.6 mmol). This reaction mixture was refluxed for 5 hours, during which time the reaction solution color changed from yellow to brown. The reaction solution was cooled to ambient temperature and poured into a stirring mixture of 1:1 ethyl acetate/ice water. The layers were separated and the ethyl acetate layer was washed sequentially with saturated sodium chloride solution (1×), 1 molar hydrochloric acid (4×), saturated sodium bicarbonate solution (1×), and again with saturated sodium chloride solution (2×). The ethyl acetate layer was then dried over magnesium sulfate, filtered, evaporated to dryness, and treated with neat pyridine (10 ml, 0.12 mole) for 1 hour. The pyridine solution was taken up in methylene chloride and washed first with 1 molar hydrochloric acid several times, then with brine solution (1×). The extract was dried over magnesium sulfate, filtered and evaporated to dryness. The resultant crude product was recrystallized by dissolution in a 7:1 ethyl acetate:cyclohexane solution and addition of a few seed crystals of the title product. Two crops of crystals were collected and gave a combined yield of 8.70 grams (29% yield) of substantially pure benzyl 7α-phenylacetamido-3-methyl-3-cephem-4-carboxylate (m.p. 169°-170° C.); i.r. (CHCl$_3$) 1773 cm$^{-1}$; n.m.r. (CDCl$_3$) δ 2.00 (s, 3, CH$_3$), 3.10, 3.37 (ABq, J=15 Hz, 2, C$_2$-H), 3.53 (s, 2, COCH$_2$Ph), 4.55 (d, J=2 Hz, 1, C$_6$-H), 4.85 (dd, J=2 and 8 Hz, 1, C$_7$-H), 5.10 (s, 2, CO$_2$CH$_2$Ph), 6.98 (d, J=8 Hz, 1, NH), 7.27, (s, 5, aromatic protons) 7.35 (s, 5, aromatic protons); u.v. (CHCl$_3$) λ$_{max}$ 264 nm (ε=8,210), o.r. [α]$_D^{25°}$ +46.9°; mass spectrum, m/e 422.

Analysis: Calculated for C$_{23}$H$_{22}$N$_2$O$_3$S: C, 65.38; H, 5.25; N, 6.63; O, 15.15; S, 7.59. Found: C, 65.25; H, 5.09; N, 6.63; O, 14.88; S, 7.44.

PREPARATION 3

Diphenylmethyl 7α-phenylacetamido-2α-methoxy-3-methyl-3-cephem-4-carboxylate

To a solution of diphenylmethyl 7α-phenylacetamido-3-methyl-3-cephem-4-carboxylate (2.88 g, 5.8 mmol) in 40 ml of methanol and 60 ml of methylene chloride, was added N-chlorosuccinimide (882 mg, 6.6 mmol) and the mixture was stirred for 90 minutes at room temperature. The reaction solution was then washed with brine (2×), dried over magnesium sulfate, filtered, and the solvent was evaporated under reduced pressure. The resultant yellow foam (2.84 g) was chromatographed over 100 grams of silica gel employing 10-15% of ethyl acetate in toluene as the eluting solvent. The first fraction to elute from the column was the desired 2α-methoxy cephem compound which was subsequently recrystallized from a mixture of ethyl acetate and cyclohexane to give pure diphenylmethyl 7α-phenylacetamido-2α-methoxy-3-methyl-3-cephem-4-carboxylate. (638 mg, 21% yield) (mp 144°-145° C.) i.r. (CHCl$_3$) 1780, 1725 and 1680 cm$^{-1}$; n.m.r. (CDCl$_3$) δ 1.95 (s, 3, CH$_3$) 3.35 (s, 3, OCH$_3$), 3.45 (s, 2, CH$_2$Ph), 4.60 (s, 1, C$_2$-H), 4.70 (d, J=2 and 8 Hz, 1, C$_7$-H), 4.85 (d, J=2 Hz, 1, C$_6$-H) 6.95 (s, 1, CH$_2$Ph), 7.3 (m, 16, aromatic and N-H); u.v. (CHCl$_3$) λ$_{max}$ 264 nm (ε=9726).

Analysis: Calculated for C$_{30}$H$_{28}$N$_2$O$_5$S: C, 68.16; H, 5.34; N, 5.30; S, 6.07. Found: C, 68.36; H, 5.33; N, 5.29; S, 5.90.

PREPARATION 4 p-Methylphenyl 4R[1-(diphenylmethyl 2-N-3-methyl-4-ol-z-but-2-ene-oate)-2-oxo-3S-phenylacetamido azetidine]disulfide p-Methylphenyl 4R[1-(diphenylmethyl 2-N-3-methyl-4-al-Z-but-2-ene-oate)-2-oxo-3S-phenylacetamido azetidine]disulfide (766 mg, 1.2 mmol) was dissolved in 20 ml of tetrahydrofuran (THF) followed by the addition of 2 ml in water. The pH of this solution was adjusted to 3.5 by the addition of a 1 molar THF solution of sodium hydroxide. Sodium cyanoborohydride (63 mg, 1.32 mmol) was added to the reaction solution, and the solution was stirred at ambient temperature for 2 hours, all the while maintaining the pH of the solution between 3.2 and 3.6 by additions of an acidic solution (3 ml. of 1 molar hydrochloric acid and 3 ml of acetic acid in 20 ml of THF). At the end of two hours the reaction solution was poured into a solution consisting of 75 ml of saturated sodium chloride solution and 50 ml of ethyl acetate, and the resulting suspension was stirred for ten minutes. The ethyl acetate layer from this solution was separated and washed in sequence with water, saturated sodium bicarbonate solution (1×), water (1×), saturated sodium chloride solution (1×), dried over magnesium sulfate, filtered and evaporated to dryness. The solid remaining after evaporation was absorbed onto 3.5 grams of silica, and chromatographed on 10 grams of silica using, in sequence, 100 ml of toluene, 200 ml of 5% ethyl acetate in toluene, 150 ml of 10% ethyl acetate in toluene and 100 ml each of 15%, 20%, 25% and 30% ethyl acetate in toluene. The final fraction collected contained the desired alcohol p-methylphenyl 4R[1-(diphenylmethyl 2-N-3-methyl-4-ol-Z-but-2-ene-oate)-2-oxo-3S-phenylacetamido azetidine]disulfide. (116 mg, 15% yield) n.m.r. (CDCl$_3$) δ 2.00 (S, 3, CH$_3$), 2.30 (s, 3, toluyl -CH$_3$), 2.88 (br. s., 1, OH), 3.41, 3.90 (ABq, J=13 Hz, 2, CH$_2$OH), 3.47 (s, 2, CH$_2$Ph), 4.62 (dd, J=3 and 8 Hz, 1, C$_3$-H) 5.17 (d, J=3 Hz, 1, C$_4$-H), 6.32 (d, J=8 Hz, 1, NH), 6.97 (s, 1, CHPh$_2$), 7.25 (m, 19, aromatic protons).

PREPARATION 5

7α-Phenylacetamido-3-methyl 1-oxa β-lactam diphenylmethyl ester

The following reaction was carried out in an inert atmosphere (N$_2$) until after evaporation of the reaction solution. p-Methylphenyl 4R[1-(diphenylmethyl 2-N-3-methyl-4-ol-Z-but-2-ene-oate)-2-oxo-3S-phenylacetamido azetidine]disulfide (0.1 g, 0.16 mmol) was dissolved in 5 ml of dried acetonitrile. Bis(trifluoroacetato)mercury(II) (136 mg, 0.32 mmol) was added to the reaction solution and the solution was stirred at ambient temperature for 0.5 hour, during which time the color of the reaction solution changed from yellow to orange. The solution was evaporated to dryness, and the resulting solid was dissolved in ethyl acetate. This ethyl acetate solution was washed with water (1×), sodium bicarbonate solution (2×), sodium chloride solution (1×), dried over magnesium sulfate, filtered then evaporated to dryness. The resultant solid was chromatographed on a preparatory-scale thin layer chromatography plate using a 1:1 solution of ethyl acetate in hexane as the eluant, yielding the pure 7α-phenylacetamido-3-methyl 1-oxa β-lactam diphenylmethyl ester compound (37 mg, 49% yield) (mp 190°–191°), i.r. (CHCl$_3$) 1780 cm$^{-1}$; n.m.r. (d$_6$-acetone) δ 1.93 (s, 3, CH$_3$), 3.6 (s, 2, CH$_2$Ph), 4.35 (br. s, 2, C$_2$-H), 4.73 (J=1.5 and 9 Hz, 1, C$_7$-H), 4.99 (d, J=1.5 Hz, 1, C$_6$-H), 6.89 (s, 1, CHPh$_2$), and 7.3 (m, 16, aromatic H and N-H); mass spectrum, m/e 406; u.v. λ$_{max}$ 263 nm (ε=6,072).

PREPARATION 6

7β-Phenylacetamido-7α-methoxy-3-methyl 1-oxa β-lactam diphenylmethyl ester

7α-Phenylacetamido-3-methyl 1-oxa β-lactam diphenylmethyl ester (121 mg, 0.25 mmol) was added to a suspension of lithium methoxide in 5 ml of dry THF (made by adding 1 ml dry methanol to 5.8 mg, 0.83 mmol of lithium in THF) under positive N$_2$ pressure at −70° C. tert-Butyl hypochlorite (0.0356 ml, 0.315 mmol) was added to this solution which was then stirred for 30 minutes at −70° C., at the end of which time trimethylphosphite (0.0075 ml) and then glacial acetic acid (0.0626 ml) were added to the solution to quench the reaction. The reaction mixture was allowed to warm to ambient temperature, evaporated to dryness, and the residue was dissolved in ethyl acetate/water solution and washed sequentially with 1 molar hydrochloric acid solution (1×), brine (1×), 5% sodium bicarbonate solution (1×), water (1×), and brine (1×). The washed solution was dried over magnesium sulfate, filtered and then evaporated to dryness to give a white foam of the product 7β-phenylacetamido-7α-methoxy-3-methyl 1-oxa β-lactam diphenylmethyl ester (123 mg). Recrystallization from acetone gave white crystals, (mp. 187°–187.5° C.) (88% yield): i.r. (CHCl$_3$) 1780 cm$^{-1}$; n.m.r. (d$_6$-acetone) δ 1.99 (s, 3, CH$_3$), 3.46 (s, 3, OCH$_3$), 3.68 (s, 2, CH$_2$Ph), 4.34 (br. s, 2, C$_2$-H), 5.05 (s, 1, C$_6$-H), 6.91 (s, 1, CHPh$_2$), and 7.3 (m, 16, aromatic H and N-H); mass spectrum, m/e 512.

PREPARATION 7

7β-Phenylacetamido-7α-methoxy-3-methyl 1-oxa β-lactam acid

7β-Phenylacetamido-7α-methoxy-3-methyl 1-oxa β-lactam diphenylmethyl ester (50 mg, 0.01 mmol) was dissolved in 0.1 ml of anisole, cooled to 0° C., and trifluoroacetic acid (0.4 ml) was slowly added to the reaction mixture. The reaction mixture was stirred for 10 minutes at 0° C., diluted with ethyl acetate, evaporated at ambient temperature, and the resulting colorless oil was taken up in 20 ml of ethyl acetate at 0° C. Ten ml of water at 0° C. was added to the ethyl acetate solution, the resulting slurry's pH was adjusted to pH 8 with 0.04 molar sodium hydroxide solution and the layers were then separated. Ten ml of ethyl acetate at 0° C. was added to the water layer, and the resulting slurry's pH was adjusted to pH 3.0 (at 0° C.) with 0.04 molar hydrochloric acid. The layers were separated, and the ethyl acetate layer was washed with saturated sodium chloride solution (1×), dried over magnesium sulfate, filtered and evaporated to dryness. The crude product was recrystallized from acetone to give pure 7β-phenylacetamido-7α-methoxy-3-methyl 1-oxa β-lactam acid (20 mg, 59% yield) (mp 169°–170° C.): i.r. (KBr) 1782 cm$^{-1}$; n.m.r. (d$_6$-acetone) δ 2.00 (s, 3, CH$_3$), 3.43 (s, 3, OCH$_3$), 4.39 (br. s, 2, C$_2$-H) 5.07 (s, 1, C$_6$-H), 5.70 (br. s, 1, COOH), and 7.33 (s, 5, aromatic H), and 7.95 (s, 1, N-H).

We claim:
1. A compound of the formula;

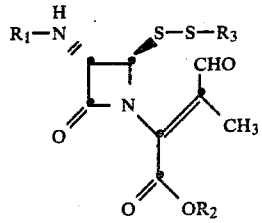

wherein R$_1$ is an acyl group of the formula

wherein R' is
(a) C$_1$-C$_7$ alkyl, cyanomethyl, C$_1$-C$_6$ haloalkyl, 4-protected amino-4-protected carboxybutyl; or
(b) C$_1$-C$_6$ alkoxy, phenoxy, benzyloxy or 4-methoxybenzyloxy; or
(c) the group —R″ wherein R″ is phenyl or substituted phenyl wherein the substituents are 1 or 2 halogens, protected hydroxy, cyano, trifluoromethyl, C$_1$-C$_4$ alkyl, C$_1$-C$_4$ alkoxy, protected carboxy, protected carboxymethyl, protected hydroxymethyl or protected aminomethyl; or
(d) an arylalkyl group of the formula R''—(O)$_m$—CH$_2$— wherein R'' is as defined above, and m is 0 or 1; or
(e) a substituted arylalkyl group of the formula

wherein R''' is R'' as defined above, 2-thienyl, 3-thienyl, 2-furyl or 3-furyl; W is protected hydroxy, protected carboxy, protected amino; or
(f) a heteroarylmethyl groups of the formula

R''''—CH$_2$— wherein R'''' is 2-thienyl, 3-thienyl, 2-furyl, 3-furyl, 2-thiazolyl, 5-tetrazolyl, 1-tetrazolyl;
R$_2$ is a carboxy protected group and R$_3$ is phenyl or a mono-substituted phenyl group, where the substituents are chloro, methoxy, methyl, or acetoxy.

2. The compound of claim 1 wherein R$_2$ is diphenylmethyl, t-butyl, p-methoxybenzyl, 2,4,6-trimethylbenzyl, trityl, 4-methoxytrityl, 4,4'-dimethoxytrityl, 4,4',4''-trimethoxytrityl.

3. The compound of claim 1 wherein R$_3$ is phenyl or p-methylphenyl.

4. The compound of claim 1 wherein R$_1$ is an acyl group of the formula

wherein R' is
(a) C$_1$–C$_7$ alkyl, cyanomethyl;
(b) C$_1$–C$_6$ alkoxy
(c) benzyl, 1-phenoxymethyl, 1-p-methoxyphenylmethyl, (d) 2-thienylmethyl, 3-thienylmethyl 2-furylmethyl, 3-furylmethyl, 2-thiazolylmethyl, 5-tetrazolylmethyl, 1-tetrazolylmethyl;
(e) 1-protected hydroxy-1-phenylmethyl, 1-protected amino-1-phenylmethyl, 1-protected amino-1-(4-protected hydroxyphenyl)methyl.

5. The compound of claim 4 wherein R$_3$ is phenyl or p-methylphenyl.

6. The compound of claim 5 wherein R$_2$ is diphenylmethyl, tert-butyl, p-methoxybenzyl, 2,4,6-trimethylbenzyl, trityl, 4-methoxytrityl, 4,4'-dimethoxytrityl and 4,4',4''-trimethoxytrityl.

7. The compound of claim 6 wherein R$_2$ is diphenylmethyl.

8. The compound of claim 1 wherein R$_1$ is an arylalkyl acyl group of the formula

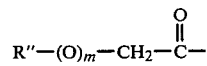

wherein R'' is phenyl or substituted phenyl wherein the substituents are 1 or 2 halogens, protected hydroxy, cyano, trifluoromethyl, C$_1$–C$_4$ alkyl, C$_1$–C$_4$ alkoxy, protected carboxy, protected carboxymethyl, protected hydroxymethyl or protected aminomethyl; and m is 0 or 1.

9. The compound of claim 8 wherein R$_3$ is phenyl or p-methylphenyl.

10. The compound of claim 9 wherein R$_2$ is diphenylmethyl, tert-butyl, p-methoxybenzyl, 2,4,6-trimethylbenzyl, trityl, 4-methoxytrityl, 4,4'-dimethoxytrityl, 4,4',4''-trimethoxytrityl.

11. The compound of claim 10 wherein R$_1$ is benzoyl.

12. The compound of claim 11 wherein R$_2$ is diphenylmethyl.

13. The compound of claim 12 wherein R$_3$ is phenyl.

14. The compound of claim 12 wherein R$_3$ is p-methylphenyl.

* * * * *